United States Patent [19]
Or et al.

[11] Patent Number: 5,508,397
[45] Date of Patent: Apr. 16, 1996

[54] ACTIVATED MACROLACTAMS

[75] Inventors: Yat S. Or; Jay R. Luly, both of Libertyville, Ill.

[73] Assignee: Abbott Laboratories, Abbott Park, Ill.

[21] Appl. No.: 357,568

[22] Filed: Dec. 16, 1994

Related U.S. Application Data

[63] Continuation of Ser. No. 100,650, Jul. 30, 1993, abandoned.
[51] Int. Cl.$^6$ .......................... C07D 498/16; C12P 17/18
[52] U.S. Cl. .......................................... 540/456; 540/452
[58] Field of Search ............................ 540/456; 514/452

[56] References Cited

U.S. PATENT DOCUMENTS

| | | | |
|---|---|---|---|
| 4,894,366 | 1/1990 | Okuhara et al. | 540/452 |
| 4,929,611 | 5/1990 | Okuhara et al. | 540/456 |
| 5,162,334 | 11/1992 | Goulet et al. | 540/456 |
| 5,189,042 | 2/1993 | Goulet et al. | 540/456 |
| 5,208,228 | 5/1993 | Ok et al. | 540/456 |
| 5,208,241 | 5/1993 | Ok et al. | 540/456 |
| 5,262,533 | 11/1993 | Sinclair et al. | 540/456 |

FOREIGN PATENT DOCUMENTS

| | | | |
|---|---|---|---|
| WO91/13889 | 9/1991 | WIPO | 540/456 |
| WO93/04680 | 3/1993 | WIPO | 540/456 |

OTHER PUBLICATIONS

Petros, et al., J. Med. Chem. 35 2467 (1992).

Primary Examiner—Robert T. Bond
Attorney, Agent, or Firm—Andreas M. Danckers; Steven R. Crowley

[57] ABSTRACT

Activated macrolactam compounds having the formula

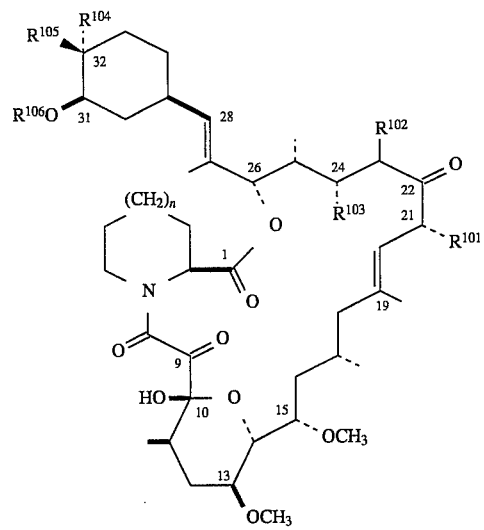

wherein n is zero or one, $R^{101}$ is selected from the group consisting of methyl, ethyl, allyl, propyl and cyclopropylmethyl;

$R^{102}$ is hydrogen, and $R^{103}$ is selected from the group consisting of hydrogen, hydroxy and a protected hydroxy group or, taken together, $R^{102}$ and $R^{103}$ form a bond;

$R^{104}$ and $R^{105}$ are chosen such that one is hydrogen while the other is -OS(O)$_2$F; and $R^{106}$ is selected from the group consisting of hydrogen, a protected hydroxy group, loweralkyl, alkenyl, cycloalkyl, aryl and arylalkyl, as well as processes for making such compounds and methods for their use in the preparation of C-32-modified derivatives of ascomycin or the congeners or analogs thereof.

5 Claims, No Drawings

ACTIVATED MACROLACTAMS

This is a continuation of U.S. patent application Ser. No. 08/100,650, filed Jul. 30, 1993 now abandoned.

FIELD OF THE INVENTION

The present invention relates to a process and intermediates for the preparation of novel chemical compounds having immunomodulatory activity, and in particular to semi-synthetic analogs of ascomycin, FK-506 and other immunosuppressant macrolactams.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. However, unsatisfactory side-effects associated with cyclosporine, such as nephrotoxicity, have led to a continued search for immunosuppressant compounds having improved efficacy and safety.

Recently, several classes of macrocyclic compounds having potent immunomodulatory activity have been discovered. Okuhara et al., in European Patent Application No. 184162, published Jun. 11, 1986, disclose a number of macrocyclic compounds isolated from the genus Streptomyces. The immunosuppressant FK-506, isolated from a strain of S. tsukubaensis, is a 23-membered macrocyclic lactone represented by formula 1a, below. Other related natural products, such as FR-900520 (1b) and FR-900523 (1c), which differ from FK-506 in their alkyl substituent at C-21, have been isolated from S. hygroscopicus yakushimnaensis. Yet another analog, FR-900525, produced by S. tsukubaensis, differs from FK-506 in the replacement of a pipecolic acid moiety with a proline group.

FR-900520, also known as ascomycin, has been previously disclosed by Arai et al. in U.S. Pat. No. 3,244,592, issued Apr. 5, 1966, where the compound is described as an antifungal agent. Monaghan, R.L., et al., on the other hand, describe the use of ascomycin as an immunosuppressant in European Patent Application No. 323865, published Jul. 12, 1989.

Although the immunosuppressive activity of FK-506 has been clinically confirmed, toxicity in mammals has limited its utility. The activity of FK-506 has, however, prompted efforts to discover novel analogs of FK-type compounds which possess superior properties. These efforts include the chemical modification of these macrocycles, including the preparation of small synthetic fragments of FK-type derivatives; a thermal rearrangement of a variety of derivatives of FK-506 which expands the macrocyclic ring by two carbons; and modifications which include methyl ether formation at the C-32 and/or C-24 positions, oxidation of the C-32 alcohol to a ketone, and epoxide formation at the C-9 position.

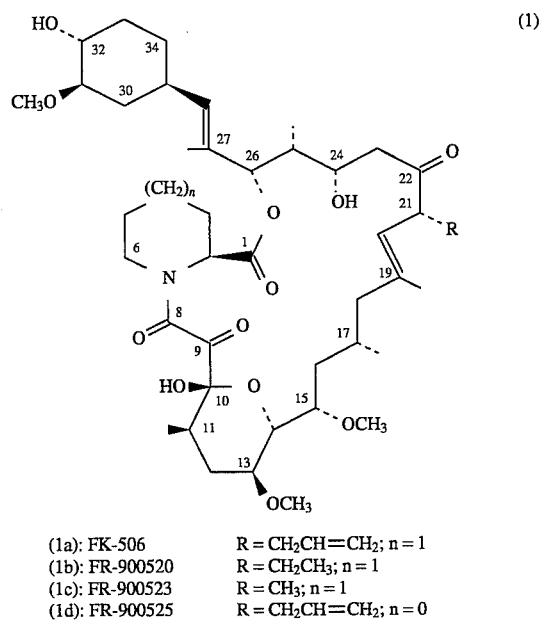

| | |
|---|---|
| (1a): FK-506 | R = $CH_2CH=CH_2$; n = 1 |
| (1b): FR-900520 | R = $CH_2CH_3$; n = 1 |
| (1c): FR-900523 | R = $CH_3$; n = 1 |
| (1d): FR-900525 | R = $CH_2CH=CH_2$; n = 0 |

Chemical derivatization of FK-type compounds at the C-32 position has been an especially promising area of research. There is therefore an ongoing need for chemical syntheses and intermediates by means of which such derivatives may be prepared. Accordingly, an object of the present invention is to provide synthetic processes for the preparation of C-32-modified FK-type compounds from starting materials obtained, directly or indirectly, by fermentation. A further object of the invention is to provide novel chemical intermediates which are useful in such synthetic processes.

SUMMARY OF THE INVENTION

It has now been discovered that C-32 derivatives of ascomycin and other FK-type compounds may be readily synthesized via activated macrolactam intermediates having a fluorosulfonyl group at the C-32 position. Accordingly, in one aspect of the present invention are disclosed compounds of the formula

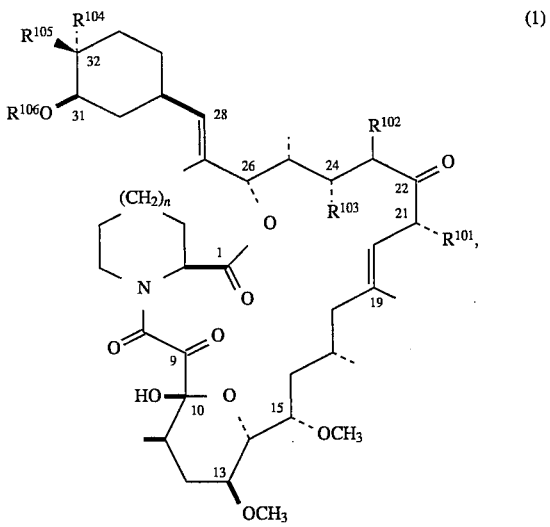

in which n is zero or one, $R^{101}$ is methyl, ethyl, allyl, propyl or cyclopropylmethyl;
$R^{102}$ is hydrogen, and $R^{103}$ is hydrogen, hydroxy or a protected hydroxy group; alternatively, $R^{102}$ and $R^{103}$, taken together, may form a C-23/C-24 bond; $R^{104}$ and $R^{105}$ are independently chosen such that one is hydrogen while the other is $-OS(O)_2F$; and $R^{106}$ is hydrogen, a protected hydroxy group, loweralkyl, alkenyl, cycloalkyl, aryl or arylalkyl.

Surprisingly, these activated macrolactam compounds are stable enough for prolonged storage, yet will readily undergo nucleophilic displacement of the fluorosulfonyl moiety. The activated compounds may therefore be reacted with an appropriate nucleophile, under mild conditions, to produce the desired C-32 derivative. The activating fluorosulfonyl group offers a particular advantage over previously-reported activating groups such as methanesulfonyl, toulenesulfonyl and camphorsulfonyl (see, for example, the published European Patent Application No. EP 184 162) in that it allows the C-32 substitution of FK-type compounds with radicals possessing a wide range of nucleophilicity in good yield. Accordingly, in another aspect of the present invention are disclosed methods for the use of the above activated FK-type macrolactams, involving the further derivatization of such compounds at the C-32 position by nucleophilic displacement reaction.

Moreover, the reaction by which the activated compounds are prepared is highly selective for the C-32 position, despite the presence of two other hydroxy groups at the C-10 and C-24 positions. As a consequence of this unexpected selectivity, the C-10 and C-24 hydroxy radicals need not be protected during activation; however, the presence of hydroxyprotecting groups at the C-10 and/or C-24 positions does not interfere with formation of the activated compounds. Accordingly, in yet another aspect of the present invention are disclosed processes for the preparation of the compounds of formula (I), comprising reacting an appropriate FK-type compound with fluorosulfonyl anhydride in concentrations and under conditions suitable for the formation of the corresponding 32-fluorosulfonyl compounds. Hydroxy radicals other than the C-32 hydroxy group may be protected by a hydroxyprotecting group prior to this reaction; alternatively, protection reactions may be carried out following the activation step.

DETAILED DESCRIPTION OF THE INVENTION

The activated intermediates of the present invention are formed by modification of FR-900520 (ascomycin) or one of its congeners (such as FK-506, etc.) by fiuorosulfonylation of the C-32 hydroxy group. Optional modifications of the starting material at the C-23 and/or C-24 positions, and protection of the C-10 and/or C-24 hydroxy functionalities, may be carried out either before or after fluorosulfonylation.

As used throughout this specification and in the appended claims, the following terms have the meanings specified:

The term "loweralkyl" as used herein refers to a monovalent straight or branched chain hydrocarbon radical of between 1 and 12 carbon atoms including, but not limited to, methyl, ethyl, n-propyl, isopropyl, n-butyl, sec-butyl, isobutyl, tert-butyl and the like.

The term "alkenyl" as used herein refers to a monovalent straight or branched chain hydrocarbon radical of between 2 and 12 carbon atoms containing a carbon-carbon double bond including, but not limited to, ethenyl, allyl, 2-propenyl, 1-butenyl, 2-butenyl and the like.

The term "aryl" as used herein refers to a monovalent carbocyclic aromatic radical of between 6 and 18 carbon atoms optionally substituted with one, two or three loweralkyl or halogen radicals as defined below including, but not limited to, phenyl, 1- or 2-naphthyl, fluorenyl, 1,2-dihydronaphthyl, 1,2,3,4-tetrahydronaphthyl, indenyl, indanyl and the like.

The term "arylalkyl" as used herein refers to a monovalent aryl radical, as defined above, appended to a loweralkyl group as defined above including, but not limited to, benzyl, naphthylmethyl and the like.

The term "cycloalkyl" as used herein refers to a monovalent cyclic hydrocarbon radical of between 3 and 8 carbon atoms including, but not limited to, cyclopropyl, cyclobutyl, cyclopentyl, cyclohexyl and the like.

The term "halogen" as used herein refers to a monovalent radical selected from fluoro (F), chloro (Cl), bromo (Br) and iodo (I).

The term "protected hydroxy group" as used herein refers to the oxygen atom of a hydroxy radical to which has been appended one of the groups which are known in the art of organic chemistry (T.W. Greene and P.G.M. Wuts, Protective Groups in Organic Synthesis, 2nd ed., John Wiley & Son, Inc., 1991) to protect a hydroxy group against undersirable reaction during synthetic procedures and to be selectively removable including, but not limited to, dimethylthexylsilyl, trisubstituted silyl such as tris(loweralkyl)silyl (e.g., trimethylsilyl, triethylsilyl, tributylsilyl, tri-isopropylsilyl, tert-butyldimethylsilyl, tri-tertbutylsilyl, triphenylsilyl, triphenylmethyldimethylsilyl, etc.); loweralkyldiarylsilyl (e.g., methyldiphenylsilyl, ethyldiphenylsilyl, propyldiphenylsilyl, tert-butyldiphenylsilyl, etc.); triarylsilyl (e.g., triphenylsilyl, trixylylsilyl, etc.); triarylalkylsilyl (e.g., tribenzylsilyl, etc.); alkylacyl (e.g., acetyl); arylacyl (e.g., benzoyl); alkoxycarbonyl (e.g., ethoxycarbonyl); $-S(O)_2$-(loweralkyl) and $-S(O)_2$-(aryl).

In the processes of the present invention, one or more of the procedures discussed below may be employed to prepare activated FK-type compounds. Such procedures include:

(a) producing by selective activation a compound of formula (I) in which $R^{102}$ is hydrogen and $R^{103}$ is hydroxy, comprising reacting a corresponding precursor in which one of $R^{104}$ and $R^{105}$ is hydrogen and the other is hydroxy with an appropriate amount of fluorosulfonyl anhydride under conditions suitable for the production of the desired product;

(b) producing by activation and elimination a compound of formula (I) in which R 102 and $R^{103}$, taken together, form a C-23/C-24 bond, comprising reacting a corresponding precursor in which $R^{102}$ is hydrogen, $R^{103}$ is hydroxy, one of $R^{104}$ and $R^{105}$ is hydrogen and the other is hydroxy with an appropriate excess of fluorosulfonyl anhydride to produce an intermediate in which the C-24 and C-32 hydroxy groups have each been converted to $-OS(O)_2F$, followed by elimination of the R 102 and R 103 groups to form a C-23/C-24 bond, each step being carried out under conditions suitable for the production of the respective desired product; and (c) producing by selective activation and protection a compound of formula (I) in which $R^{103}$ is a protected hydroxy group, comprising reacting a corresponding precursor in which $R^{103}$ is hydroxy, one of $R^{104}$ and $R^{105}$ is hydrogen and the other is hydroxy with an appropriate amount of fluorosulfonyl anhydride to produce an intermediate in which the C-32 hydroxy group has been convened to $-OS(O)_2F$, followed by reaction of the intermediate with an appropriate protecting agent to form a C-24 protected hydroxy group, each step being carried out under conditions suitable for the production of the respective desired product.

In process (a), suitable reagent for activation of an alcohol of formula I is fluorosulfonyl anhydride (prepared according to the procedure described by S. Kongpricha, W.G. Preusse and R. Schwarer, in Inorganic Synthesis, 1968, 11, p151–155). The activation may be carried out in a solvent which does not adversely affect the reaction (e.g., diethyl ether, dichloromethane, tetrahydrofuran, chloroform or N-methylpyrrolidone or a mixture thereof). The reaction may require cooling or heating, depending on the method used. Further, the reaction is preferably conducted in the presence of an organic or inorganic base such as cesium bicarbonate, pyridine, lutidine, picoline, quinoline, diisopropylethylamine and the like. The reaction temperature is preferably from −100 to 30° C., and more preferably from −78 to 0° C. The reaction may require 20 minutes to 24 hours to complete, depending on the reagent chosen.

In process (b), suitable reagent for activation of an alcohol is more than five equivalents of fluorosulfonyl anhydride (prepared according to the procedure described by S. Kongpricha, W.G. Preusse and R. Schwarer, in Inorganic Synthesis, 1968, 11, p151–155). The activation may be carried out in a solvent which does not adversely affect the reaction (e.g., diethyl ether, dichloromethane, tetrahydrofuran, chloroform or N-methylpyrrolidone or a mixture thereof). The reaction may require cooling or heating, depending on the method used. Further, the reaction is preferably conducted in the presence of an organic or inorganic base such as cesium bicarbonate, pyridine, luffdine, picoline, quinoline, diisopropylethylamine and the like. The reaction temperature is preferably from −100 to 30° C., and more preferably from −78 to 0° C. The reaction may require 20 minutes to 24 hours to complete, depending on the reagent chosen.

In process (c), suitable protecting groups for hydroxy include those groups well known in the art are: dimethylthexylsilyl, trisubstituted silyl such as tri-lower alkylsilyl (e.g., trimethylsilyl, triethylsilyl, tributylsilyl, tri-isopropylsilyl, tert-butyldimethylsilyl, tri-tertbutylsilyl etc.); lower alkyldiarylsilyl (e.g., methyl-diphenylsilyl, ethyl-diphenylsilyl, propyldiphenylsilyl, tert-butyl-diphenylsilyl, etc.); tirarylsilyl (e.g., triphenylsilyl, tri-p-xylylsilyl, etc.); triarylalkylsilyl (e.g., tribenzylsilyl).

Suitable o-silylations may be carried out using a wide variety of organosilicon reagents such as triethylsilyl trifluoromethanesulfonate, triisopropylsilyl trifluoromethanesulfonate, tert-butyldimethylsilyl trifluoromethanesulfonate (L.N. Mander and S.P. Sethi, Tetrahedron Letter., 1984, 25, 5953) and dimethylthexylsilyl trifluoromethanesulfonate (H. Wetter and K. Oertle, Tetrahedron Lett., 1985, 26, 5515).

The reaction may be carried out in a solvent which does not adversely affect the reaction (e.g., diethyl ether, dichloromethane, tetrahydrofuran, chloroform or a mixture). The reaction may require cooling or heating, depending on the activation conditions chosen. Further, the reaction is preferably conducted in the presence of an organic or inorganic base such as cesium bicarbonate, pyridine, lutidine, picoline, quinoline, diisopropylethylamine and the like. The reaction temperature is preferably from −100 to 30° C., and more preferably from −78 to 0° C. The reaction may require 20 minutes to 24 hours to complete, depending on the reagent chosen.

In general, the methods of use of the present invention comprising reacting a compound of formula (I) with a nucleophilic agent having a nitrogen, oxygen, sulfur or carbon nucleophile to produce a derivative of the compound in which the -OS(O)$_2$F group at the C-32 position is displaced by the nucleophile. Suitable nucleophiles are those described in the literature including, e.g., J. March, Advanced Organic Chemistry, Reactions, Mechanisms and Structure, 3 ed., 1985, John Wiley & Sons, incorporated herein by reference. The nucleophilic displacement reaction may be carried out in a solvent which does not adversely affect the reaction (e.g., chloroform, dichloromethane, tetrahydrofuran, pyridine, acetone, acetonitrile or dimethylsulfoxide). The reaction may be conducted above, at, or below ambient temperature.

The compounds, processes and uses of the present invention will be better understood in connection with the following examples, which are intended as an illustration of and not a limitation upon the scope of the invention.

Example 1: Formula I:
$R^{101}$-ethyl;$R^{102}$-H;$R^{103}$-OH;$R^{104}$-OS(O)$_2$F;$R^{105}$-H; $R^{106}$-methyl.

Fluorosulfonyl anhydride (0.17 g) was added into a stirred solution of ascomycin (0.4 g) and 2,6-lutidine (0.228) in dry dichloromethane (5 mL) at −70° C. for 1 hour. The reaction mixture was partitioned between ether and ice-cold 0.1 N HCl (aq). The organic phase was washed once with brine, dried over magnesium surfate and filtered through silica gel (2 g) and eluted with ether. Solvent was removed in vacuo to yield 0.3 g of the title compound. MS (FAB) m/z: M+K=912. $^1$H NMR (CDCl$_3$, 500 MHz) δ5:4.67 (m, H-32), 3.92, 3.98 (m, H-24).

Example 2: Formula I: $R^{101}$- allyl; $R^{102}$-H;$R^{103}$-OH; $R^{104}$-OS(O)$_2$F;$R^{105}$-H; $R^{106}$-methyl.

The title compound of Example 2 is prepared from fluorosulfonyl anhydride, FK-506 and 2,6-lutidine according to the procedure described in Example 1.

Example 3: Formula I: R101- ethyl; $R^{102}$-H;$R^{103}$-tert-butyldimethylsilyloxy; R104- tert-butyldimethylsilyloxy; $R^{105}$- H;$R^{106}$- methyl.

Tert-Butyldimethylsilyl chloride (47.64 g) was added portionwise into a solution of ascomycin (25 g) and imidazole (43 g) in dry N,N-dimethylformamide (500 mL) and stirred at room temperature for 24 hours. The solvent and excess tert-butyldimethylsilyl chloride were removed by distillation (35° C. bath) under high vacuum. The solid residue was partitioned between ethyl acetate and saturated ammonium chloride, brine and dried over magnesium sulfate. The solvent was removed in vacuo and solid residue purified by silica gel chromatography (1 kg) eluting with 5% acetone/hexanes. Yield: 27 g. MS (FAB) m/z: M+K=1058.

Example 4: Formula I: R101- ethyl; $R^{102}$-H; $R^{103}$-tert-butyldimethylsilyloxy, $R^{104}$- OH; $R^{105}$=H; $R^{106}$- methyl.

Hydrogen fluoride (48% aq, 5 mL) was added into a stirred solution of the title compound of Example 3 (32 g) in acetonitrile (500 mL) at 0° C. After being stirred at room temperature for 1.5 hours, the reaction mixture was cooled to 0° C. Powdered sodium bicarbonate (10 g) was added to the cooled reaction mixture and stirred for an additional hour. Solid was removed by filtration and solvent removed in vacuo. The residue was partitioned between ethyl acetate (500 mL) and 10% sodium bicarbonate (3×300 mL). The organic phase was washed with brine (250 mL), dried over magnesium sulfate and solvent removed in vacuo. The product was purified by silica gel chromatography eluting with 25% acetone/hexanes. Yield: 24.3 g. MS (FAB) m/z:

$M+K=844$.

Example 5; Formula I: $R^{101}$- ethyl; $R^{102}$-H; $R^{103}$-tert-butyldimethylsilyloxy, $R^{104}$-OS(O)$_2$F: $R^{105}$-H; $R^{106}$-methyl.

The title compound was prepared from the title compound of Example 4 (0.5 g) and fluorosulfonyl anhydride (0.12 mL) and 2,6-lutidine (0.26 mL) in dichloromethane (5 mL) according to the procedure described in Example 1. Yield: 0.53 g, 97%. MS (FAB) m/z: $M+K=1026$.

Example 6: Formula I: $R^{101}$-ethyl; $R^{102}$-H; $R^{103}$-triisopropysilyloxy, $R^{104}$-OS(O)$_2$F: $R^{105}$-H; $R^{106}$-methyl.

Triisopropylsilyl trifluoromethanesulfonate (0.2 g) is added into a stirred solution of the title compound of Example 1 (0.1 g) and lutidine (0.1 g) in dry dichloromethane (2 mL) at −70° C. The reaction is stirred at 0° C. for 1 hour after addition. The reaction mixture is partitioned between ether and ice-cold 0.1 N HCl (aq). The organic phase is washed once with brine, dried over magnesium sulfate and filtered through silica gel and eluted with ether. The product is obtained by removal of solvent in vacuo.

Example 7: Formula I: $R^{101}$- ethyl; $R^{102}$ and $R^{103}$ taken together form a bond, $R^{104}$-OH; $R^{105}$-H; $R^{106}$-methyl.

The title compound was prepared according to the methods described in the published European Patent Application No. EP 192 668 of Fisons, page 26, Example 11: m.p. 124°–125° C., MS (FAB) m/z: $M+NH_4=791$.

Example 8; Formula I: $R^{101}$-ethyl; $R^{102}$-H; $R^{103}$-H; $R^{104}$-OH; $R^{105}$-H; $R^{106}$-methyl.

The title compound of Example 7 (1 g) was combined with 10% palladium on carbon (0.1 g) in methanol and reduced under hydrogen (1 atm) for 4 hours. The catalyst was removed by passing the mixture through a filter agent and the filtrate was concentrated under reduced pressure. The crude was purified by flash chromatography on silica gel eluting with 25% acetone in hexanes to supply the title compound (348 mg) as colorless foam: MS (FAB) m/z: $M+K=814$.

Example 9: Formula I: $R^{101}$-ethyl; $R^{102}$-H; $R^{103}$-H $R^{104}$-OS(O)$_2$F; $R^{105}$-H; $R^{106}$-methyl.

The title compound is prepared from the title compound of Example 8 and fluorosulfonyl anhydride according to the procedure described in Example 1.

Example 10: Formula I: $R^{101}$-ethyl; $R^{102}$ and $R^{103}$ taken together form a bond, $R^{104}$-OS(O)$_2$F; $R^{105}$-H; $R^{106}$, methyl.

Procedure (A):

The title compound is prepared from the title compound of Example 7 and fluorosulfonyl anhydride according to the procedure described in Example 1.

Procedure (B):

The title compound is prepared from ascomycin and 5 equivalents of fluorosulfonyl anhydride and excess 2,6-lutidine according to the procedure described in Example 1.

Example 11: Formula I: $R^{101}$-ethyl; $R^{102}$-H; $R^{103}$-OH; $R^{104}$ and $R^{105}$ taken together form an oxo group; $R^{106}$-methyl.

Methylsulfide-chlorine complex was prepared by adding oxalyl chloride (0.32 g) into a stirred solution of dimethylsulfoxide (0.44 g) in dichloromethane (4 mL) and stirred at −70° C. for 0.5 hour. The solution of the complex was added in slow dropwise fashion into a stirred solution of ascomycin (1.6 g) in dichloromethane (5 mL) at −70° C. After being stirred for 20 minutes, triethylamine (1.4 g) was added. Stirring was continued at −70° C. for 0.5 hour and room temperature for 1 hour. The reaction mixture was partitioned between ether and 1N hydrochloric acid. The organic phase was washed with brine and dried over magnesium sulfate, and the solvent removed in vacuo. The product was purified by silica gel chromatography (70 g) eluting with ether. Yield: 0.95 g. MS (FAB) m/z: $M+H=790$.

Example 12: Formula I: $R^{101}$- ethyl; $R^{102}$-H; $R^{103}$-OH; $R^{104}$-H; $R^{105}$-OH; $R^{106}$-methyl.

Lithium tri-tert-butoxyaluminum hydride (0.2 mL, 1 M in THF) was added slowly into a stirred solution of the title compound of Example 11 (0.056 g) in dry THF (1 mL) at −70° C. under nitrogen. After being stirred at −70° C. for 3 hours, the reaction mixture was partitioned between ether and 1 N HCl (aq). The organic phase was dried over magnesium sulfate and solvent removed in vacuo. The product was purified by preparative TLC (35% acetone in hexanes). Yield: 0.025 g. MS (FAB) m/z: $M+K=830$.

Example 13; Formula I; $R^{101}$-ethyl; $R^{102}$-H; $R^{103}$-OH; $R^{104}$-H; $R^{105}$-OS(O)$_2$F; $R^{106}$-methyl.

The title compound is prepared from the title compound of Example 12 and fluorosulfonyl anhydride according to the procedure described in Example 1.

Example 14: Formula I: $R^{101}$-ethyl; $R^{102}$-H; $R^{103}$-tert-Butyldimethylsiloxy; $R^{104}$-H; $R^{105}$-3-Piperidinopropylamino: $R^{106}$-methyl.

3-Piperidino-1-propylamine (0.06 g) was added into a stirred solution of the title compound of Example 5 (0.2 g) in acetonitrile (1.5 mL) at 0° C. After being stirred at room temperature overnight, the product was purified by reverse phase HPLC (C18 column, 41.4 mm ID, Dynamax-60A) eluting with aqueous acetonitrile containing 1% trifluoroacetic acid. Yield: 8%. MS (FAB) m/z: $M+H=1030$, $M+K=1068$.

Example 15; Formula I: $R^{101}$-ethyl; $R^{102}$-H; $R^{103}$-OH; $R^{104}$-H; $R^{105}$-3-piperidinopropylamino: $R^{106}$-methyl.

A solution of HF (0.4 mL 48% aquous HF in 1 mL of acetonitrile) was added into a stirred solution of the title compound of Example 14 (0.11 g). After being stirred at room temperature, the product was purified by reverse phase HPLC (C18 column, 41.4 mm ID, Dynamax-60A) eluting with aqueous acetonitrile containing 1% trifluoroacetic acid. Yield: 66%. MS (FAB) m/z: $M+H=915$, $M+K=954$.

Example 16: Formula I: $R^{101}$-ethyl: $R^{102}$-H;$R^{103}$-OH;$R^{104}$-3-piperidinopropylamino; $R^{105}$-H;$R^{106}$-methyl.

The title compound is prepared from the title compound of Example 13 and 3-piperidino-1-propylamine in acetonitrile according to the procedure described in Example 14.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses and/or methods of use of the invention, may be made without departing from the spirit and scope thereof.

We claim:

1. A compound having the formula

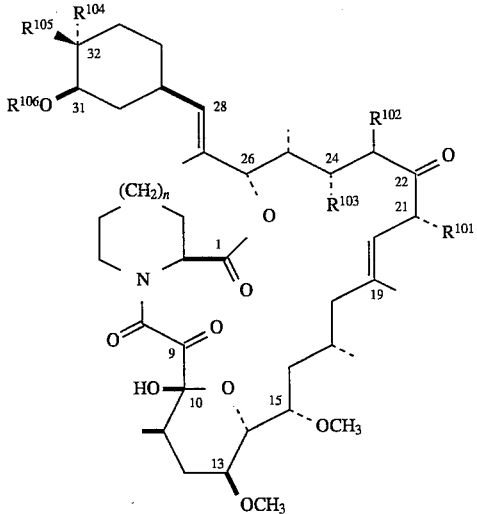

wherein n is zero or one, $R^{101}$ is selected from the group consisting of methyl, ethyl, allyl, propyl and cyclopropylmethyl;

$R^{102}$ is hydrogen, and $R^{103}$ is selected from the group consisting of hydrogen, hydroxy and a protected hydroxy group or, taken together, $R^{102}$ and $R^{103}$ form a bond, wherein a protected hydroxy group is a hydroxy group which is protected by a protecting group selected from tris($C_1$-$C_{12}$-loweralkyl)silyl, (di(aryl))($C_1$-$C_{12}$-loweralkyl)silyl, tri(aryl)silyl, tri(aryl-$C_1$-$C_{12}$-alkyl)silyl, $C_1$-$C_{12}$-alkyl-C(O)-, aryl -C(O)-, $C_1$-$C_{12}$-alkyl-OC(O)-, -S(O)$_2$-($C_1$-$C_{12}$-loweralkyl) and -S(O)$_2$-(aryl);

$R^{104}$ and $R^{105}$ are chosen such that one is hydrogen while the other is -OS(O)$_2$F; and $R^{106}$ is selected from the group consisting of hydrogen, $C_1$-$C_{12}$-loweralkyl, $C_2$-$C_{12}$-alkenyl, $C_3$-$C_8$-cycloalkyl, aryl, aryl-$C_1$-$C_{12}$-alkyl and a hydroxy protecting group selected from tris($C_1$-$C_{12}$-loweralkyl)silyl, (di(aryl))$C_1$-$C_{12}$-loweralkyl)silyl, tri(aryl)silyl, tri(aryl-$C_1$-$C_{12}$-alkyl_silyl, $C_1$-$C_{12}$-alkyl-C(O)-, aryl -C(O)-, $C_1$-$C_{12}$-alkyl-OC(O)-, -S(O)$_2$-($C_1$-$C_{12}$-loweralkyl) and -S(O)$_2$-(aryl); wherein at each occurrence aryl is independently selected from phenyl, 1-naphthyl, 2-naphthyl, fluorenyl, 1,2-dihydronaphthyl, 1,2,3,4-tetrahydronaphthyl, indanyl and indenyl and the aryl group can be unsubstituted or substituted with one, two or three substitutents independently selected from $C_1$-$C_{12}$-loweralkyl and halogen.

2. A compound of the formula

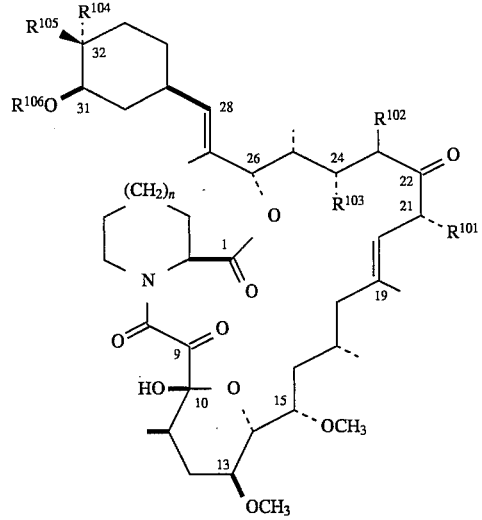

wherein n is 0 or 1 and (a) $R^{101}$ is ethyl, $R^{102}$ is hydrogen, $R^{103}$ is hydroxy, $R^{104}$ is fluorosulfonyl, $R^{105}$ is hydrogen and $R^{106}$ is methyl;

(b) $R^{101}$ is allyl, $R^{102}$ is hydrogen, $R^{103}$ is hydroxy, $R^{104}$ is fluorosulfonyl, $R^{105}$ is hydrogen and $R^{106}$ is methyl;

(c) $R^{101}$ is ethyl, $R^{102}$ is hydrogen, $R^{103}$ is tert-butyldimethylsilyloxy, $R^{104}$ is fluorosulfonyl, $R^{105}$ is hydrogen and $R^{106}$ is methyl;

(d) $R^{101}$ is ethyl, $R^{102}$ is hydrogen, $R^{103}$ is triisopropylsilyloxy, $R^{104}$ is fluorosulfonyl, $R^{105}$ is hydrogen and $R^{106}$ is methyl;

(e) $R^{101}$ is ethyl, $R^{102}$ is hydrogen, $R^{103}$ is hydrogen, $R^{104}$ is fluorosulfonyl, $R^{105}$ is hydrogen and $R^{106}$ is methyl;

(f) $R^{101}$ is ethyl, $R^{102}$ and $R^{103}$ taken together form a bond, $R^{104}$ is fluorosulfonyl, $R^{105}$ is hydrogen and $R^{106}$ is methyl; or (g) $R^{101}$ is ethyl, $R^{102}$ is hydrogen, $R^{103}$ is hydroxy, $R^{104}$ is hydrogen, $R^{105}$ is fluorosulfonyl and $R^{106}$ is methyl.

3. A process for the preparation of a compound according to claim 1 in which $R^{102}$ is hydrogen and $R^{103}$ is hydroxy, comprising reacting a corresponding precursor in which one of $R^{104}$ and $R^{105}$ is hydrogen and the other is hydroxy with an appropriate amount of fluorosulfonyl arthydride under conditions suitable for production of the compound.

4. A process for the preparation of a compound according to claim 1 in which $R^{102}$ and $R^{103}$, taken together, form a C-23/C-24 bond, comprising the steps of (a) reacting a corresponding precursor in which $R^{102}$ is hydrogen, $R^{103}$ is hydroxy, one of $R^{104}$ and $R^{105}$ is hydrogen and the other is hydroxy with an appropriate excess of fluorosulfonyl arthydride to produce an intermediate in which the C-24 and C-32 hydroxy groups have each been converted to -OS(O)$_2$F, under conditions suitable for production of the intermediate; and (b) treating the intermediate to eliminate the C-23 hydrogen and C-24 -OS(O)$_2$F groups to form a C-23/C-24 bond, under conditions suitable for production of the compound.

5. A process for the preparation of a compound according to claim 1 in which $R^{103}$ is a protected hydroxy group as defined therein, comprising the steps of (a) reacting a corresponding precursor in which $R^{103}$ is hydroxy, one of $R^{104}$ and $R^{105}$ is hydrogen and the other is hydroxy with an appropriate amount of fluorosulfonyl anhydride to produce an intermediate in which only the C-32 hydroxy group has been converted to $-OS(O)_2F$, under conditions suitable for production of the intermediate; and (b) reacting the intermediate with an appropriate protecting agent to form a C-24 protected hydroxy group, under conditions suitable for production of the compound.

* * * * *

UNITED STATES PATENT AND TRADEMARK OFFICE
CERTIFICATE OF CORRECTION

PATENT NO. : 5,508,397
DATED : April 16, 1996
INVENTOR(S) : Y. S. Or and J. R. Luly It is certified that error appears in the above-indentified patent and that said Letters Patent is hereby corrected as shown below:

Column 9, line 64, change "alkyl_silyl" to --alkyl)silyl--.

Column 10, line 52, change "arthydride" to --anhydride--.

Column 10, line 60, change "arthydride" to --anhydride--.

Signed and Sealed this

Twenty-sixth Day of November 1996

Attest:

BRUCE LEHMAN

Attesting Officer     Commissioner of Patents and Trademarks